United States Patent [19]
Jefferies

[11] Patent Number: 5,948,426
[45] Date of Patent: Sep. 7, 1999

[54] METHOD AND ARTICLE TO INDUCE HEMATOPOIETIC EXPANSION

[76] Inventor: Steven R. Jefferies, 3692 Wingfield Dr., York, Pa. 17402

[21] Appl. No.: 09/070,686

[22] Filed: Apr. 30, 1998

Related U.S. Application Data

[60] Provisional application No. 60/045,520, May 3, 1997.

[51] Int. Cl.[6] ................ A61F 2/28; A61K 9/19; A61K 38/18; C12N 5/08
[52] U.S. Cl. .......... 424/423; 424/426; 424/484; 424/486; 424/93.7; 435/373; 435/372; 435/374; 435/395; 435/405; 514/8
[58] Field of Search ................. 424/423, 426, 424/484, 486, 93.7; 514/8; 435/373, 372, 374, 395, 405

[56] References Cited

U.S. PATENT DOCUMENTS

| | | | |
|---|---|---|---|
| 4,322,398 | 3/1982 | Reiner et al. | 424/19 |
| 4,394,370 | 7/1983 | Jefferies | 424/15 |
| 4,472,840 | 9/1984 | Jefferies | 3/1.9 |
| 5,393,739 | 2/1995 | Bentz et al. | 514/12 |
| 5,405,772 | 4/1995 | Ponting | 435/240.31 |
| 5,459,069 | 10/1995 | Palsson et al. | 435/289.1 |
| 5,461,034 | 10/1995 | Rodan et al. | 514/14 |
| 5,604,204 | 2/1997 | Ammann et al. | 514/12 |
| 5,605,822 | 2/1997 | Emerson et al. | 435/172.3 |
| 5,631,219 | 5/1997 | Rosenthal et al. | 514/6 |
| 5,635,387 | 6/1997 | Fei et al. | 435/378 |
| 5,643,789 | 7/1997 | Ducheyne et al. | 435/402 |
| 5,648,301 | 7/1997 | Ducheyne et al. | 501/39 |
| 5,650,299 | 7/1997 | Lawman et al. | 435/70.7 |
| 5,681,559 | 10/1997 | DiGiusto et al. | 424/93.1 |
| 5,705,149 | 1/1998 | Namen et al. | 424/85.2 |
| 5,707,962 | 1/1998 | Chen et al. | 514/12 |
| 5,716,827 | 2/1998 | Tsukamoto et al. | 435/325 |
| 5,728,581 | 3/1998 | Schwartz et al. | 435/385 |

*Primary Examiner*—David Saunders
*Assistant Examiner*—F. Pierre VanderVegt
*Attorney, Agent, or Firm*—Renner, Kenner, Greive, Bobak, Taylor & Weber

[57] ABSTRACT

An article and method to create retrievable sites of implantable and transplantable bone marrow, in a human or animal recipient, by implanting bone-marrow inducing conjugates of collagen and demineralized freeze-dried bone allograft (DFDBA) into accessible soft or hard tissue sites is provided. The implantation of such collagen-DFDBA conjugate grafts into suitable ectotrophic sites results in the formation of bone-marrow and hematopoietic tissue within the implant. By removing all or a portion of the bone marrow containing areas of the implant, an additional source of hematopoietic tissue and bone marrow cells is formed which can subsequently be transplanted into the same individual as an autograft, or a related or compatible individual as an allograft.

34 Claims, No Drawings

METHOD AND ARTICLE TO INDUCE HEMATOPOIETIC EXPANSION

CROSS REFERENCE TO RELATED APPLICATIONS

This application claims the benefit of U.S. Provisional Patent Application No. 60/045,520 filed May 3, 1997.

TECHNICAL FIELD OF THE INVENTION

The present invention relates generally to the production of implantable bone marrow, bone marrow cells, and hematopoietic tissue in mammals. More particularly, the present invention relates to the creation of retrievable sites of implantable bone marrow in tissue culture or in a human or animal recipient, by the use of bone marrow inducing conjugate composites of collagen and demineralized freeze-dried bone allograft.

BACKGROUND OF THE INVENTION

Over the past decade, Bone Marrow Transplantation (BMT) has evolved from an experimental procedure reserved for patients with refractory leukemia into a rapidly expanding area of clinical investigation that offers high cure rates for patients with aplastic anemia, acute and chronic leukemia, and selected types of lymphoma. The objective of BMT is to provide a healthy stem cell population that will differentiate into blood cells to replace deficient or pathologic cells of the host.

There currently exist two generally accepted procedures for bone marrow transplantation. The first and most common procedure is allogenic bone marrow transplantation in which bone marrow is obtained by aspiration from the iliac crests of an HLA-compatible donor and infused into the patient requiring the healthy hematopoietic marrow. The procedure in which the bone marrow is aspirated through a puncture site into the iliac crest is very painful to the donor and sometimes obtains limited quantities of useful, transplantable hematopoietic tissue.

The second option for BMT involves autologous transplantation (ABMT); namely removal of a patient's own marrow for safe keeping when the patient is free of disease or when a complete remission has been induced by radiation and chemotherapy, or by other therapeutic means, followed by ablative treatment of the patient with the hope of destruction of any residual tumor and rescue with the patient's own bone marrow. Since an autograft is used, no immunosuppression is necessary and graft versus host disease (graft rejection) is minimal. Because the autologous "rescued" bone marrow can produce mature blood cells quickly, ABMT allows patients to tolerate very high doses of chemotherapy with less risk of infection and bleeding. Nevertheless, the success of autologous BMT is strictly dependent on obtaining sufficient quantities of healthy bone marrow from the patient-host during a period of tumor remission and when healthy hematopoietic tissue is present and obtainable. Although ABMT has some therapeutic advantages, it remains a difficult, somewhat risky, and expensive procedure.

While graft versus host disease (implant rejection) and infections are both issues in BMT, the major limiting factor in the use of BMT is the availability of sufficient quantities of healthy, immunologically compatible bone marrow tissue with sufficient hematopoietic activity, which in turn results from a lack of suitable donors. Since only 25 to 30% of patients have a sibling who can serve as an HLA-compatible donor, alternatives need to be found.

Clearly, there exists a need to make the procedure for the retrieval of bone marrow for transplantation more accessible, less painful (i.e., avoid puncture of the iliac crest and the associated morbidity), increase the availability of useful bone marrow and bone marrow cells, and control more easily the microenvironment around the implant to enhance bone marrow formation while potentially removing or eliminating tumor cells and other undesirables in the bone marrow as well.

OBJECTS OF THE INVENTION

It is therefore an object of the present invention to provide a source of bone marrow, bone marrow components such as bone marrow cells, and hematopoietic tissue for autologous transplantation or for use as an allograft.

It is another object of the present invention to provide a conjugate composite of collagen-demineralized freeze-dried bone allograft suitable for implantation in soft and hard tissue sites.

It is another object of the invention to provide such a conjugate composite which will allow the formation of bone marrow in soft and hard tissue sites in a patient/host, such that later access and retrieval of bone marrow, bone marrow cells, bone marrow components, stem cells, and hematopoietic tissue is possible.

It is still another object of the invention to provide such a conjugate composite which may additionally contain other compatible biopolymers, macromolecules, growth factors, compounds, vitamins, and minerals which can enhance the structure and function of the bone marrow producing implant.

It is a further object of the invention to provide such a conjugate composite which may be incorporated within, attached to, or augmented by additional structures or design features which enhance implantation or access to the implant and the bone marrow containing portion(s) of the implant.

It is an additional object of the invention to provide a method of producing additional ectotrophic sites of bone marrow production in a human or animal host by implanting the appropriate conjugate composite implant materials, allowing the in-situ development of bone marrow calls, and retrieving all or part of the bone marrow containing tissue or cells by aspiration, incision within the implant, or excision of the entire implant.

It is an additional object of the invention to use retrieved bone marrow tissue and cells from the conjugate implant for autologous transplantation into the host from which they were obtained, or alternatively, allogenically transplanted into another histocompatible individual host requiring bone marrow augmentation or replacement.

It is an additional object of the invention to provide a conjugate composite collagen-demineralized freeze-dried bone allograft (DFDBA) implant which can be seeded with appropriate stem cells, then implanted in a suitable host to facilitate bone marrow production.

It is an additional object of the invention to provide a conjugate composite collagen-DFDBA implant which can be seeded with appropriate stem cells, then placed in a tissue culture reactor to facilitate in-vitro formation of bone marrow or precursor tissue.

These and other object(s) of the invention, which will become apparent from the disclosure to follow, are carried out by the invention as hereafter described.

SUMMARY OF THE INVENTION

The present invention provides a conjugate composite and a method of using the composite to create retrievable sites of implantable bone marrow, bone marrow components such as bone marrow cells, and hematopoietic tissue in a human or animal recipient, by implanting bone-marrow inducing conjugates of collagen and demineralized freeze-dried bone allograft (DFDBA) into accessible soft or hard tissue sites. The implantation of such collagen-DFDBA conjugate grafts into suitable ectotrophic sites results in the formation of bone-marrow and hematopoietic tissue within the implant. Alternatively, the conjugate composite may be grown in-vitro such as in tissue culture to yield the implantable bone marrow material.

By utilizing all or a portion of the bone-marrow containing portion of the implant, such as by removal of the bone marrow material from tissue culture or from the host human or animal, the source of hematopoietic tissue that had been formed can subsequently be transplanted into the host individual as an autograft, or into a related/compatible individual as an allograft.

The conjugate composites of the present invention include collagen-DFDBA conjugates, either in the presence or in the absence of other biopolymers. According to the invention, other growth factors or substances which aid in the formation or accelerate the formation of bone marrow and hematopoietic tissue can be added in various ways to these collagen-DFDBA conjugate composites.

The present invention further provides the incorporation of access ports or windows in or on the implant itself, to facilitate the ability to withdraw bone marrow components, or alternatively, to add additional implant material or growth factors/enhancement substances to the implant before or after implantation.

Methods according to the invention include preparing the implant, inserting the implant into a suitable soft or hard tissue site, retrieving bone marrow, bone marrow components and hematopoietic material from the implant (or alternatively, completely removing the implant with its bone marrow compartment), and associated appropriate procedures for maintaining the bone marrow containing implant.

A bone marrow inducing conjugate composite according to the present invention comprises from about 10 to about 90 parts by weight of demineralized freeze-dried bone matrix (DFDBA) and from about 90 to about 10 parts by weight of collagen, preferably in the form of reconstituted collagen. The DFDBA may be in the form of particles of various sizes and shapes which may be incorporated into the collagen matrix of the conjugate. Both the collagen and the DFDBA may be from a human or animal source.

In a preferred embodiment, the present invention provides a bone marrow inducing conjugate composite comprising from about 10 to about 90 parts by weight of demineralized freeze-dried bone matrix (DFDBA), from about 90 to about 10 parts by weight of collagen, and an amount effective to initiate bone marrow differentiation of at least one of (a) mammalian stem cells, (b) bone marrow components, and (c) a growth factor.

The present invention further provides a method of producing bone marrow material in vitro comprising ex vivo culturing the above conjugate composite. In another embodiment, the present invention provides a method for producing bone marrow material in vivo comprising implanting the above conjugate composite in at least one of a soft tissue and hard tissue site and maintaining the conjugate composite implant for a period of time sufficient to induce the formation of at least one of bone marrow, bone marrow cells, and hematopoietic tissue within the implant.

According to certain embodiments of the invention, other biopolymers or structures may be incorporated into or may surround the implant itself, including structures made of synthetic resorbable polymers which may be incorporated in the collagen-DFDBA conjugate matrix, and structures of fabricated biocompatible polymers such as tubes, entry-ports, or membranes which may be incorporated into or surround the collagen-DFDBA conjugate material. Biocompatible metals such as titanium or titanium alloy in various configurations, such as tubes or mesh for example, may also be incorporated in the implantation conjugate to facilitate access, retrieval, or sampling.

A method is provided according to the present invention, for producing an ectotrophic site for bone marrow material in a human or animal suitable for allogenic or autogenous Bone Marrow Transplantation (BMT) comprising:

(a) placing a bone marrow producing implant comprising collagen and a bone marrow inducing material in a suitable site within soft tissue or adjacent to hard tissue; and (b) maintaining the implant in its implanted site for a period of time sufficient to induce the formation of at least one of bone marrow, bone marrow cells, bone marrow components, hematopoietic tissue, stem cells, and ectopic viable bone within the implant.

The invention further includes accessing the implant to retrieve at least one of bone marrow, bone marrow cells, bone marrow components, hematopoietic tissue, stem cells, and ectopic viable bone, such as by removing at least a portion of the implant.

The implantation procedure of Step (a) above may include injection of liquid, gel, or solid compositions. Alternatively, the implant may be inserted into the appropriate body cavity or location by conventional incision and surgical implantation procedures. The removal of all or a portion of the implant as described above may include, but is not limited to, aspiration of the bone marrow containing portion of the implant, as well as incision or excision of the implant or portions of the implant.

Another method according to the invention includes the preparation of the collagen-DFDBA conjugate composite implants to be capable of culturing and growing bone marrow cells outside of a human or animal host altogether. The collagen-DFDBA is fabricated to accept the seeding of human stem cells and other bone marrow components, to permit the culturing and growing of bone marrow cells and hematopoietic tissue. Sufficient amounts of implantable bone marrow for transplantation could be cultured using this method.

PREFERRED EMBODIMENTS OF THE INVENTION

The bone marrow producing composite according to the invention is a mixture of collagen and demineralized freeze-dried bone allograft (DFDBA). One preferred composite has from about 10 to about 90 parts by weight of DFDBA and from about 90 to about 10 parts by weight of collagen. A more preferred composite contains from about 30 to about 70 parts by weight of DFDBA. The source of both the collagen and DFDBA may be from a human or animal source (for example, bovine collagen), but the preferred composite for implantation in humans comprises collagen from a bovine source, and DFDBA from human origin. A more preferred composite is composed of collagen from a human source, for example human tendon, and DFDBA from a human source as well.

Collagen is used as the binding matrix and main structural component of the bone marrow producing composite material for several reasons. Reconstituted collagen has demonstrated excellent histocompatibility without antibody formation or graft rejection in numerous in vivo implantation studies. Reconstituted collagen can be fabricated into porous sponge-like structures which allow unimpeded cellular ingrowth. Collagen is the natural biomaterial which constitutes from 50 to 70% by weight of bone organic matrix. Reconstituted collagen has demonstrated the ability to bind both large and small molecular weight macromolecules, and complexation with collagen protects these macromolecules from denaturation due to environmental influences.

The actual collagen-DFDBA conjugate composite can be fabricated in various forms including but not limited to: injectable gels, membranes, powders, lyophilized sponges with various degrees of porosity, or combinations of these various forms. The conjugate material can be fabricated according methods and procedures described in U.S. Pat. Nos. 4,394,370 and 4,472,840, both of which are incorporated herein by reference as if fully rewritten below.

Alternatively, an acidic or alkaline collagen dispersion, either from human or animal sources, can be lyophilized by conventional methods. This lyophilized mass can then be ground into a powder with various degrees of coarseness. The grinding of the lyophilized mass is preferably performed under cooling by the use of dry-ice and/or liquid nitrogen. This collagen powder can then be dry blended with various ratios of demineralized freeze-dried bone allograft (DFDBA), also preferably in a powder or particulate form.

After blending, the powder mixture can be hydrated with sufficient sterile distilled water to form a uniform dispersion. A small amount of ethanol may be added to the sterile distilled water, which is used to rehydrate the powder blend. This blended collagen/demineralized freeze-dried bone allograft dispersion may then be lyophilized into a sponge configuration. This sponge configuration may be used as the implant. Alternatively, the lyophilized conjugate sponge can be re-ground into a powder, and this conjugate powder can be used as the implant material (for example, by being dispersed into an appropriate vehicle such as a common medical excipient, and the resulting dispersion being injected into the transplant site.

Examples of such excipients include, but are not limited to, polyols, glycerin, propylene glycol, vegetable oils, purified peanut oil, proteins, protein hydrogels, blood proteins, albumin, fibrin, collagen gel, collagen solution, gelatin, pluronic ot tetronic surfactants or copolymers, hydroxy methyl cellulose and cellulose derivatives, ultrapure alginate such as sodium alginate, biocompatible carbohydrates, sugars, and polymers derived therefrom, dextran suitable for injection, and the like.

In a preferred form of the method for inducing the formation, expansion and retrieval of bone marrow and hematopoietic tissue, a human collagen-human DFDBA sponge implant is implanted in a soft tissue site, either within connective tissue, fat cells, or muscle tissue, using a subcutaneous surgical implantation technique. Accessible sites in or adjacent to hard tissue or bony sites may also be used for implantation. Alternatively, the sponge implant may be configured into a thin cylinder implant which could be injected or inserted subcutaneously. The implant may be inserted in or adjacent to bone, for example, so as to affix the implant to the bone for structural stability. However, it is preferred that the implant be placed in soft tissue, such as muscle tissue.

The implant is permitted to remain in-situ for periods of from about two to about three (2–3) weeks to about nine to about twelve (9–12) months or longer, to permit the formation of bone marrow tissue within the implant. If positioned in a highly accessible location, the implant may be radiographed to more precisely define potential bone marrow containing areas of the implant.

When the collagen-DFDBA conjugate composite is implanted in the body, the implant initially becomes vascularized. As a vascular bed is established in the differentiated bone, stem cells are supplied to the implant, and bone marrow begins to form. When the collagen-DFDBA conjugate composite is cultured ex vivo, stem cells or other bone marrow inducing factors must be introduced to initiate bone marrow development. The incorporation, however, of stem cells and/or growth factors in the implanted conjugate composite results in the accelerated and increased development of the bone marrow components.

Examples of growth factors that are suitable for the expansion of hematopoietic tissue in the collagen-DFDBA conjugate composites of the present invention include, but are not limited to, interleukin-4, interleukin-6, interleukin-7, platelet-derived growth factor, alpha interferon species, tumor necrosis factor (TNF), TGF-beta and TNF-alpha proteins, colony-stimulating factors, such as granulocyte colony-stimulating factor, stem cell proliferation factor, osteogenic growth polypeptide, autocrine growth factor, and the like, and their combinations.

The retrieval of the bone marrow can be accomplished through the complete removal of the implant, with the excised implant being manipulated ex-situ to remove the bone marrow containing tissue and cells. Alternatively, a probe or catheter may be introduced into the implant while still in-situ in the patient, and bone marrow containing tissue and cells may be aspirated. Regardless of how the bone marrow is removed from the implant, the retrieved bone marrow tissue and cells may then be suitably processed, by means known in the medical art and sciences, prior to transplantation in the host or in the patient needing the hematopoietic tissue or bone marrow.

Other biopolymers or structures are advantageously incorporated into or may surround the implant itself. Structures made of various well-known synthetic resorbable polymers, including but not limited to polymers of polylactic or polyglycolic acid, or various co-polymers of lactic and glycolic acid, may be incorporated in the collagen-DFDBA conjugate matrix. Inorganic or organic fillers of various types may also be incorporated in the conjugate composite. These polymers and fillers can serve a structural function, to aid in retaining a porous, geometrically stable structure to the implant, to serve as a growth site for the bone marrow. The polymers and fillers may also be resorbable, to provide components to the implant to assist in the production of osseous or marrow components.

Structures such as tubes, entry-ports, or membranes may be incorporated into or surround the collagen-DFDBA conjugate material implant. These structures may be fabricated from biocompatible polymers such as silicone, ethylene-vinyl acetate copolymer, and the like. Titanium or biocompatible titanium alloys in various configurations, such as tubes or mesh for example, may also be incorporated in the conjugate composite implant to facilitate access to or retrieval of the implant or the produced bone marrow material, or sampling of the bone marrow material product. Other biocompatible metals such as tantalum, or biopolymer coated or encapsulated metals can also be used.

New ectotrophic sites for the production of bone marrow material in a human or animal, suitable for allogenic or autogenous Bone Marrow Transplantation (BMT), are prepared by the method comprising placing, such as by implanting, a bone marrow producing implant comprising collagen and a bone marrow inducing material or substance, such as demineralized freeze-dried bone allograft, or Bone Morphogenetic Protein(s) (BMP), in a suitable soft or hard tissue location; maintaining or allowing the implant to remain in its implanted site for a period of time sufficient to induce the formation of bone marrow within the implant; and removing all or a portion of the implant to retrieve, all or in part, the bone marrow, bone marrow cells, and hematopoietic tissue.

The implantation procedure discussed above may include injection of a liquid, gel, or solid collagen-DFDBA conjugate material. Alternatively, the implant may be placed or inserted into the appropriate body cavity or location by conventional incision and surgical implantation procedures. The removal of all or a portion of the implant as described above may include, but is not limited to, aspiration of the bone marrow containing portion of the implant, as well as incision or excision of the implant or portions of the implant.

The above method for producing and maintaining bone marrow producing implants may be modified to permit the injection or addition of growth factors such as colony stimulating factor, or other cytokines, antibiotics, vitamins, and/or minerals, directly to the implant prior to implantation or while it is in-situ. The implant, prior to implantation or upon removal from the implanted site, may be seeded with human stem cells and placed in appropriate tissue culture media within a suitable bioreactor or sterile container to facilitate further growth and maturation of the bone marrow tissue and cells. Additionally, this procedure permits the capability to rinse or clean the removed implant, or portions of the implant, with an appropriate medium to remove tumor cells or other undesirables in the bone marrow grown within the implant. The collagen-DFDBA implant can be processed in the form of a porous sponge to permit perfusion of various sterile liquids and media to rinse or clean the implant and its marrow components.

Another method according to the invention involves the use of these collagen-DFDBA conjugate implants to be capable of culturing and growing bone marrow cells outside of a human or animal host altogether. The collagen-DFDBA can be fabricated to accept the seeding of human stem cells and other bone marrow components to permit the culturing and growing of bone marrow cells and hematopoietic tissue. Sufficient amounts of implantable bone marrow for transplantation into a patient could be cultured using this method.

EXAMPLE 1

A bone marrow inducing implant is configured in such a manner that the implant is enclosed in an appropriate biocompatible polymer which can partially isolate or partition the implant from the surrounding soft or hard tissue. This polymer encasement can be composed of a non-resorbable biocompatible polymer, such as medical grade silicone, medical grade polyurethane, Ultra-High Molecular Weight Polyethylene (UHMWPE), or expanded Teflon (PTFE), just to list several non-limiting examples of operable polymeric materials. The bone marrow inducing implant can also be enclosed entirely or partially in a resorbable or semi-resorbable polymer. Examples of appropriate bioresorbable polymers are those derived from various combinations of known lactide and/or glycolide polymers. Various entrance and exit ports can be configured in the outer casting and within the implant itself to gain access to the marrow components and vascular elements which are induced within the hematopoietic tissue.

EXAMPLE 2

The outer polymeric casing of the bone marrow inducing implant is fabricated from a radiodense or radioopaque material. Such a coating or partition can serve to reduce exposure of the implant to radiation of various types to which the patient may be subjected for diagnosis and/or treatment purposes. Such radiation shielding of the expanded hematopoietic tissue preserves a source of bone marrow for later transplantation to replace marrow depleted as a result of radiation treatment. The radiodense surface layer or coating also aids in identification of the implant location by presenting a clear radioopaque image on conventional radiographs.

Shielding the conjugate composite implant from diagnostic or therapeutic radiation exposure can include substantially enclosing the conjugate composite implant in a radiation shielding material, or shielding the conjugate composite implant externally to the body. In addition to the use of biopolymers for this purpose, the shield can be in the form of a biocompatible metal which is dense enough to block the radiation, or a metal which is contained in a biopolymer, such as by a coating or encapsulation.

EXAMPLE 3

The bone marrow inducing implant of the present invention, in addition to providing a source of ectopic autogenous bone marrow, can also provide a source of additional autogenous and viable bone. When an additional source of viable autogenous bone is required, but is in otherwise short supply, additional implanted sites of collagen-DFDBA or collagen-BMP implants, with or without additional growth factors; can be implanted in selected sites for sufficient time periods to allow later retrieval of mature autogenous bone for transplantation into autogenous recipient sites. Such implants provide the benefits of autografts without the limits of autograft availability.

EXAMPLE 4

The ability of the bone inducing implants of the present invention to form vascularized tissue and actual microscopic blood vessels within the internal implant space, also provides an excellent vehicle for parentially introducing drugs and growth factors of various types. Drugs can be injected directly into the implant itself, thereby serving as a drug delivery reservoir. Alternatively, access ports and channels provided into the implant itself could serve the dual role of not just retrieving stems cells and marrow, but also permitting the introduction of drugs and growth factors for local and systemic application and treatment. The implant can then serve as a unique drug delivery vehicle or conduit for local or systemic delivery of pharmaceutical drugs, growth factors, and a wide range of therapeutic agents.

Thus, the objects of the invention are accomplished by the present invention, which is not limited to the specific embodiments described above, but which includes variations modifications and equivalent embodiments defined by the following claims.

I claim:

1. A bone marrow inducing conjugate composite comprising from about 10 to about 90 parts by weight of demineralized freeze-dried bone matrix (DFDBA), from about 90 to about 10 parts by weight of collagen, and one selected from the group consisting of (a) mammalian stem cells, (b) bone marrow components, and (c) a growth factor in an amount effective to induce bone marrow differentiation within said conjugate composite.

2. The bone marrow inducing conjugate composite of claim 1 wherein the conjugate composite comprises from about 30 to about 70 parts by weight of DFDBA and from about 70 to about 30 parts by weight of collagen.

3. The bone marrow inducing conjugate composite of claim 1 wherein at least one of the collagen and the DFDBA is from a human source.

4. The bone marrow inducing conjugate composite of claim 1 wherein the stem cells are from at least one of a human host and a human histocompatible with the host.

5. The bone marrow inducing conjugate composite of claim 1 wherein the conjugate composite additionally comprises at least one biopolymer incorporated into or surrounding the conjugate composite.

6. The bone marrow inducing conjugate composite of claim 5 wherein the at least one biopolymer is a non-resorbable polymer.

7. The bone marrow inducing conjugate composite of claim 5 wherein the at least one biopolymer includes a structure selected from the group consisting of tubes, ports, membranes, and combinations thereof.

8. The bone marrow inducing conjugate composite of claim 5 wherein the at least one biopolymer is a resorbable polymer.

9. The bone marrow inducing conjugate composite of claim 5 wherein the at least one biopolymer is a semi-resorbable polymer.

10. The bone marrow inducing conjugate composite of claim 1 implanted in or adjacent to hard tissue of a host.

11. A method of producing bone marrow material in vitro comprising ex vivo culturing the conjugate composite of claim 1.

12. A method for producing bone marrow material in vivo comprising implanting the conjugate composite of claim 1 in at least one selected from the group consisting of a soft tissue and hard tissue site and maintaining the conjugate composite implant for a period of time sufficient to induce the formation of at least one selected from the group consisting of bone marrow, bone marrow cells, bone marrow components, hematopoietic tissue, stem cells and ectopic viable bone within the implant.

13. The method of claim 12 including shielding the conjugate composite implant from diagnostic or therapeutic radiation exposure, wherein said shielding comprises one selected from the group consisting of (a) substantially enclosing the conjugate composite implant in a radiation shielding material and (b) shielding the conjugate composite implant externally to the body.

14. The method of claim 12 including introducing at least one selected from the group consisting of additional conjugate composite material, a growth factor, a growth enhancement substance, a pharmacological drug, and a therapeutic agent.

15. The method of claim 12 including accessing the conjugate composite implant to retrieve at least one selected from the group consisting of bone marrow, bone marrow cells, bone marrow components, hematopoietic tissue, stem cells, and ectopic viable bone.

16. The method of claim 12 wherein said implanting includes at least one selected from the group consisting of (a) injecting the conjugate composite in one form selected from the group consisting of liquid, gel and solid, and (b) an incision or surgical implantation procedure.

17. The bone marrow inducing conjugate composite of claim 1 wherein the conjugate composite has associated therewith at least one biocompatible metal or biopolymer-contained metal structure selected from the group consisting of tubes, ports, mesh, shields, and combinations thereof.

18. The bone marrow inducing conjugate composite of claim 1 implanted in soft tissue of a host.

19. A method for producing an ectotrophic site for bone marrow material in a human or animal suitable for allogenic or autogenous bone marrow transplantation comprising:
 (a) placing a bone marrow producing implant comprising collagen and a bone marrow inducing material in a suitable site within soft tissue or adjacent to hard tissue; and
 (b) maintaining the implant in its implanted site for a period of time sufficient to induce the formation of at least one selected from the group consisting of bone marrow, bone marrow cells, bone marrow components, hematopoietic tissue, stem cells, and ectopic viable bone within the implant.

20. The method of claim 19 wherein the implant comprises a conjugate composite of from about 10 to about 90 parts by weight of demineralized freeze-dried bone matrix (DFDBA) and from about 90 to about 10 parts by weight of collagen.

21. The method of claim 20 wherein the conjugate composite comprises from about 30 to about 70 parts by weight of DFDBA and from about 70 to about 30 parts by weight of collagen.

22. The method of claim 20 wherein at least one of the collagen and the DFDBA is from a human source.

23. The method of claim 20 wherein the conjugate composite includes stem cells from at least one of a human host and a human histocompatible with the host.

24. The method of claim 20 wherein the conjugate composite additionally comprises at least one biopolymer incorporated into or surrounding the conjugate composite.

25. The method of claim 24 wherein the at least one biopolymer is a non-resorbable polymer.

26. The method of claim 24 wherein the at least one biopolymer includes a structure selected from the group consisting of tubes, ports, membranes, and combinations thereof.

27. The method of claim 20 wherein the conjugate composite has associated therewith at least one biocompatible metal or biopolymer-contained metal structure selected from the group consisting of tubes, ports, mesh, shields, and combinations thereof.

28. The method of claim 19 including introducing into the implant at least one selected from the group consisting of a bone marrow inducing material, a growth factor, a growth enhancement substance, a pharmacological drug, and a therapeutic agent.

29. The method of claim 19 wherein said soft tissue is at least one selected from the group consisting of connective tissue, fat, and muscle tissue.

30. The method of claim 19 including accessing the implant to retrieve at least one selected from the group consisting of bone marrow, bone marrow cells, bone marrow components, hematopoietic tissue, stem cells, and ectopic viable bone.

31. The method of claim 19 wherein said placing includes at least one selected from the group consisting of (a) injecting the implant in one form selected from the group consisting of liquid, gel and solid, and (b) an incision or surgical implantation procedure.

32. The method of claim 19 including shielding the implant from diagnostic or therapeutic radiation exposure, wherein said shielding comprises one selected from the group consisting of (a) substantially enclosing the implant in a radiation shielding material and (b) shielding the implant externally to the body.

33. The method of claim 22 wherein the at least one biopolymer is a resorbable polymer.

34. The method of claim 22 wherein the at least one biopolymer is a semi-resorbable polymer.

\* \* \* \* \*